United States Patent [19]

Mayer et al.

[11] 4,162,247

[45] Jul. 24, 1979

[54] BIS-(ALKYLPHENYL)-ALKANECARBOXYLIC ACID HYDRAZIDES, THEIR PREPARATION AND USE

[75] Inventors: Norbert Mayer, Gablingen; Gerhard Pfahler, Augsburg; Hartmut Wiezer, Gersthofen, all of Fed. Rep. of Germany

[73] Assignee: Hoechst Aktiengesellschaft, Frankfurt am Main, Fed. Rep. of Germany

[21] Appl. No.: 885,905

[22] Filed: Mar. 13, 1978

[30] Foreign Application Priority Data

Mar. 15, 1977 [DE] Fed. Rep. of Germany ....... 2711206

[51] Int. Cl.² .......................... C08K 5/51; C08K 5/49; C08K 5/25; C07C 103/22; C07F 9/02
[52] U.S. Cl. ............................. 260/45.9 NC; 252/404; 260/559 D; 260/923
[58] Field of Search ........... 260/559 D, 923, 45.9 NC; 252/404

[56] References Cited

U.S. PATENT DOCUMENTS

| 2,893,965 | 7/1959 | Greenlee | 260/559 D |
|---|---|---|---|
| 3,247,240 | 4/1966 | Meier et al. | 260/559 R |
| 3,285,855 | 11/1966 | Dexter et al. | 260/45.85 S |
| 3,427,345 | 2/1969 | Holmen | 260/559 D |
| 3,455,875 | 7/1969 | Mauz et al. | 260/45.9 NC |
| 3,660,438 | 5/1972 | Dexter | 260/559 H |
| 3,956,427 | 5/1976 | Schmidt | 260/923 |

FOREIGN PATENT DOCUMENTS 513041 5/1976 U.S.S.R. ................... 260/923

Primary Examiner—Veronica P. Hoke
Attorney, Agent, or Firm—Connolly and Hutz

[57] ABSTRACT

Bis-(alkylphenol)-alkanecarboxylic acid hydrazides are obtained by reaction of bisphenol-alkanecarboxylic acid chlorides, azides, anhydrides or esters with hydrazine hydrate, at a temperature of from 5 to 200° C. These hydrazides are excellent stabilizers for plastic materials, especially polyolefins.

6 Claims, No Drawings

BIS-(ALKYLPHENYL)-ALKANECARBOXYLIC ACID HYDRAZIDES, THEIR PREPARATION AND USE

For stabilizing polyolefins there are used phenolic antioxidants, as is well known. Because phenols of low molecular weight, for example, 2,5-di-tert.-butyl-4-methylphenol, are highly volatile substances, there have been developed long ago phenol-carboxylic acid esters having long-chain alkyl radicals, which, on processing of the plastic material, do not trouble the operations by bad smell.

However, such phenol-carboxylic acid esters of long-chain alcohols have a serious disadvantage: because of their fat-like character, they are easily extracted from plastic materials being in contact with oils and fats as in the case of certain packaging sheets. For this reason, polar phenolic antioxidants have been developed, such as salts of alkylated phenol-carboxylic acids (German Offenlegungsschrift No. 2,544,014).

A special class of polar antioxidants are the phenol-carboxylic acid hydrazides described for example in German Offenlegungsschrift No. 2,310,800 and U.S. Pat. Nos. 3,772,245; 3,870,680 and 3,948,854. Because of their molecular structure, that is, single electron pairs at the nitrogen and oxygen atoms and mobile protons at the nitrogen atoms, these hydrazides of carboxylic acids are efficient complex-forming agents for heavy metal ions. They are used therefore for the manufacture of plastics compositions for insulating cables, in order to suppress the destructive action of traces of metal diffused into the plastic material.

The phenol-carboxylic acid hydrazides hitherto used as stabilizers contain one mol of phenol in the carboxylic acid moiety. The preparation of such monophenol-carboxylic acids, however, is generally difficult and requires several reaction steps, and furthermore, their antioxidant action is insufficient because of the presence of only one phenol nucleus in the phenol-carboxylic acid molecule. Thus, there is still a demand for easily obtainable phenol-carboxylic acid hydrazides the antioxidant action of which is improved relative to their tendency of forming complexes with heavy metal ions.

It has been found that hitherto unknown bis-(alkylphenol)-alkanecarboxylic acid hydrazides meet the above requirements to a very large extent.

The present invention relates therefore to compounds of the formula

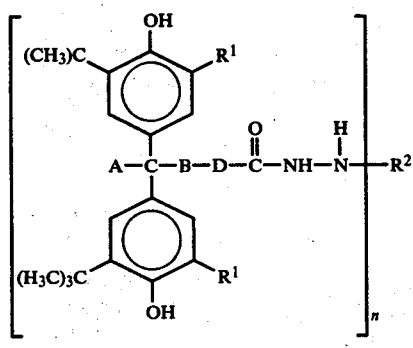

in which
n is 1, 2 or 3;
A is H or $C_1$ to $C_8$-alkyl;
B is $C_1$ to $C_8$-alkylene; or
A and B together with the carbon atom separating them are members of a cycloalkyl ring having from 5 to 12 carbon atoms;
D is a chemical bond or, in the case where

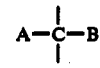

is a cycloalkyl ring, optionally a $C_1$ to $C_3$-alkylene radical;
$R^1$ is H or a $C_1$ to $C_4$-alkyl radical; and
$R^2$ is H, or, corresponding to the meaning of n, a mono-, bi- or tri-valent radical having the following structures:

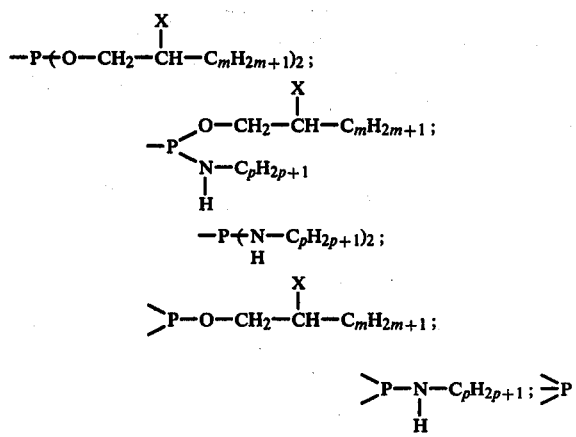

in which m is an integer of from 0 to 30, p an integer of from 10 to 20, and X is H or OH.

This invention relates furthermore to a process for the preparation of these compounds, and to their use as stabilizers in plastics processing.

The compounds of the invention have a balanced relation between the non-polar phenol and alkane radical on the one hand and the polar carboxylic acid hydrazide radical on the other hand, so that they are sufficiently compatible with the mostly non-polar plastic materials to be fully efficient as heat and, optionally, light stabilizers, and that they are substantially resistant to extraction by fats and oils to act as excellent stabilizers for plastic materials, especially polyolefins.

The phenol-carboxylic acid hydrazides of the invention are obtained in simple manner by reaction of the bisphenol-alkane-carboxylic acid chlorides, azides, anhydrides or, especially, esters with hydrazine hydrate, at temperatures of from 5° to 200° C., especially 100° to 150° C. The reaction is generally carried out without solvents; optionally, however, a solvent intert to the corresponding reactants may be present.

The open-chain or cyclic bis-(hydroxyphenyl)-alkanecarboxylic acid esters of the formula

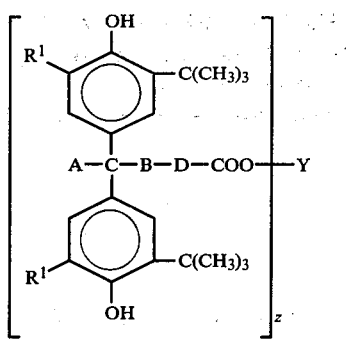

are easily obtained from the corresponding ketocarboxylic acid esters by condensation with alkylphenols (German Pat. No. 1,953,332, German Offenlegungsschrift No. 2,612,214). The symbols of the above formula have the following meanings:

A is hydrogen or an alkyl group having from 1 to 8 carbon atoms, preferably H or $CH_3$;

B is an alkylene group having from 1 to 8, preferably 1 to 3, carbon atoms;

A and B, together with the carbon atom separating them, optionally being members of a cycloalkyl ring having from 5 to 12, preferably 5 or 6, carbon atoms;

D is a chemical bond, or optionally an alkylene radical having from 1 to 3, preferably 2, carbon atoms in the case where

is a cycloalkyl ring;

$R^1$ is hydrogen or an alkyl radical having from 1 to 4 carbon atoms, preferably H or tertiary butyl;

Y is an alkyl or alkylene radical having from 1 to 4 carbon atoms; and z is 1 or 2, corresponding to the valency of Y.

Preferred bis-(hydroxyphenyl)-alkanecarboxylic acid esters are 3,3-bis-(3'-tert.-butyl-4'-hydroxyphenyl)-butanoic acid glycol diester, 3,3-bis-(3',5'-di-tert.-butyl-4'-hydroxyphenyl)-butanoic acid glycol diester, or 1,1-bis-(3'-tert.-butyl-4'-hydroxyphenyl)-cyclopentane-carboxylic acid methyl ester.

The compounds substituted at the nitrogen atom by phosphorus can be prepared by ester interchange of phosphorous acid triesters of volatile alcohols with the bis-(hydroxyphenyl)-alkanecarboxylic acid hydrazides of the invention in the presence of catalysts, for example catalytic amounts of tertiary amines or strong bases. Suitable phosphorous acid esters are tri-lower alkyl-phosphites such as tributyl phosphite, tri-propyl phosphite, preferably trimethyl phosphite or especially triethyl phosphite; triphenyl phosphite being appropriate, too. Mono-, di- or trisubstitution of phosphite is possible by using 1, 2 or 3 mols of hydrazide per mol of phosphite. Those alkoxy groups of phosphite which remain when the substitution is not complete can be transesterified with scarcely volatile alcohols or amines, especially fatty alcohols or β-hydroxy-fatty alcohols having from 2 to 30 carbon atoms and/or fatty amines having from 10 to 20 carbon atoms, which ester interchange can be carried out in one single process step by reacting mixtures of hydrazide, higher alcohol and/or amine. Thus, hydrazides are obtained the free amino group of which carries a phosphorous substituent of the following possible structures:

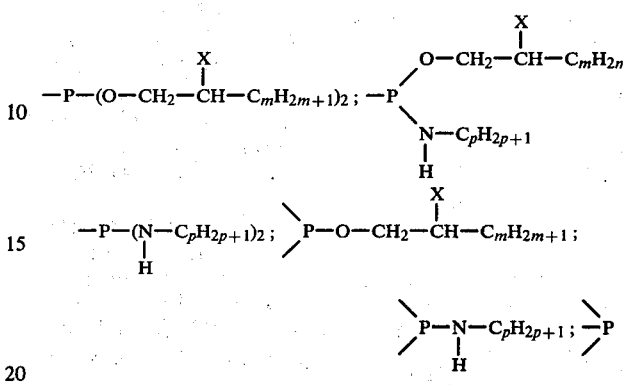

m, p and X being as defined above.

As already mentioned, the hydrazides of bis-(hydroxyphenyl)-alkanecarboxylic acids and the derivatives thereof are excellent stabilizers for synthetic polymers, preferably polyolefins such as polybutadiene or polyisoprene and especially polyethylene or polypropylene; furthermore for polystyrene, polyacrylates or polymethacrylates. They are used in amounts of from 0.001 to 5.0, preferably 0.01 to 1, % by weight relative to the polymer, and above all in those fields of application where traces or ions of heavy metals may occur, for example stemming from catalyst residues or being contained in electric insulation materials.

For stabilizing the polymers, there may be used as costabilizers further usual phenolic antioxidants, such as esters of 3,5-di-tert.-butyl-4-hydroxyphenyl-propionic acid or of 3,3-bis-(3'-tert.-butyl-4'-hydroxyphenyl)-butyric acid, together with metal salts of higher fatty acids, especially calcium stearate. In certain cases, the addition of sulfur containing costabilizers is advantageous, for example of lauryl- or stearyl-thio-dipropionate or dioctadecyl sulfide or -disulfide. Suitable phosphite costabilizers are mixed phosphite esters of pentaery-thritol or sugar alcohols with fatty alcohols such as stearyl alcohol, for example distearyl-pentaerythrityl diphosphite or tri-stearyl-sorbityl triphosphite, furthermore tristearyl phosphite, trisnonylphenyl phosphite, triphenyl phosphite or diphenyl-isooctyl phosphite. In some cases, it is recommended to use UV stabilizers in addition to the costabilizers, examples of which are hydroxybenzophenones, benzotriazoles or the highly active piperidine stabilizers known only recently.

The following examples illustrate the invention. By "hydrazine hydrate", there is to be understood in all Examples the commercial 80% aqueous solution of hydrazine hydrate.

EXAMPLE 1:

3,3-Bis-(3'-tert.-butyl-4'-hydroxy-phenyl)-butanoic acid hydrazide monohydrate 400 g (0.5 mol) of 3,3-bis-(3'-tert.-butyl-4'-hydroxyphenyl)-butanoic acid glycol diester (prepared according to German Auslegeschrift No. 1,953,333) in 400 ml of hydrazine hydrate are stirred for 6 hours in a 2 liter three-necked flask provided with agitator, gas inlet tube and reflux condenser at an oil bath temperature of 120° C. with nitrogen being passed through the mixture.

After having replaced the reflux condenser by a distilling connecting tube, the volatile reactants are distilled off. The residue is dissolved in acetic acid ethyl ester under heat, boiled with active charcoal, filtered and allowed to crystallize in the cold. 365 g (88% of the theoretical yield) of a compound having a melting point of 120° C. and the following formula are obtained

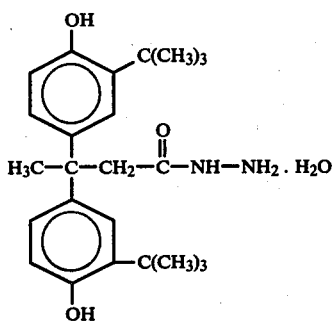

$C_{24}H_{36}N_2O_4$ (MW 416) C calc.: 69.2%; H calc.: 8.7%; found: 69.4% found: 8.9%.

EXAMPLE 2

3,3-Bis-(3',5'-di-tert.-butyl-4'-hydroxy-phenyl)-butanoic acid hydrazide 20 g of 3,3-bis-(3',5'-di-tert.-butyl-4'-hydroxyphenyl)-butanoic acid glycol diester (prepared according to German Offenlegungsschrift No. 2,503,050 or 2,615,764), together with 10 ml of hydrazine hydrate and 18 ml of water are molten in a bomb tube, and digested for 15 hours at 150° C. The crystalline residue remaining after cooling is recrystallized from toluene/heptane. 16 g (92% of the theoretical yield) of the following compound are obtained:

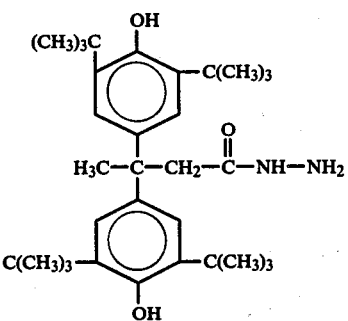

m.p. 172.5° C.

$C_{32}H_{50}N_2O_3$ (MW 510) C calc.: 75.2% H calc.: 9.8%; found: 75.3% found: 10.0%; N calc.: 5.5%; found: 5.5%.

EXAMPLE 3

3,5-Bis-(3'-tert.-butyl-4'-hydroxy-phenyl)-hexanoic acid hydrazide 300 g of 5,5-bis-(3'-tert.-butyl-4'-hydroxy-phenyl)-hexanoic acid methyl ester are refluxed with agitation for 15 hours in 400 ml of hydrazine hydrate. The reaction mixture is then poured with thorough agitation in 1 liter ½ of water and suction-filtered. The product is recrystallized from acetic acid ethyl ester. 207 g of the intended hydrazide having a melting point of 119° C. and the following formula are obtained:

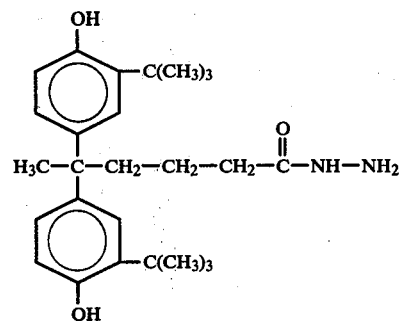

$C_{26}H_{38}N_2O_3$ (MW 426) C calc.: 73.2% H calc.: 8.9%; found: 72.9% found: 9.1%; N calc.: 6.6%; found: 6.3%.

EXAMPLE 4

1,1-Bis-(3'-tert.-butyl-4'-hydroxy-phenyl)-cyclopentane-2-carboxylic acid hydrazide 15 g of 1,1-bis-(3'-tert.-butyl-4'-hydroxy-phenyl)-cyclopentane-carboxylic acid methyl ester (prepared according to German Offenlegungsschrift No. 2,612,214) are digested with 15 ml of hydrazine hydrate for 30 hours in a bomb tube at 150° C. The reaction product is recrystallized from ether/heptane. 10.3 g of the hydrazide having a melting point of 233° C. and the following structure are obtained.

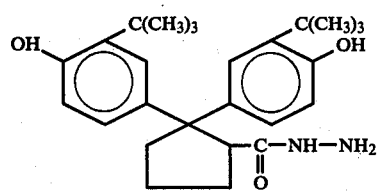

$C_{26}H_{36}N_2O_3$ (MW 424) C calc.: 73.6% H calc.: 8.5% N calc.: 6.6%; found: 73.6% found: 8.7% found: 6.3%;

EXAMPLE 5

Phosphorous acid-di-octadecyl ester-3,3-bis-(3'-tert.-butyl-4'-hydroxy-phenyl)-butanoyl-hydrazide In a 1 liter three-necked flask provided with agitator, nitrogen inlet and distilling connecting tube mounted on top of a Vigreux column, 79.6 g (0.2 mol) of 3,3'-bis-(3'-tert.-butyl-4'-hydroxyphenyl)-butanoic acid hydrazide according to Example 1, 108 g (0.4 mol) of stearyl alcohol, 35.2 ml (0.21 mol) of triethyl phosphite and 1 drop of triethylamine are stirred in a light nitrogen flow at 130° to 150° C., thus causing 34 ml of ethanol to be distilled off within 3 hours. When the development of ethanol has come to an end, excess triethyl phosphite is eliminated by establishing a water jet vacuum for a short time, and subsequently, the product is filtered via a heated pressure filter. 177 g of the compound having the following formula and a drop point of 69° C. are obtained.

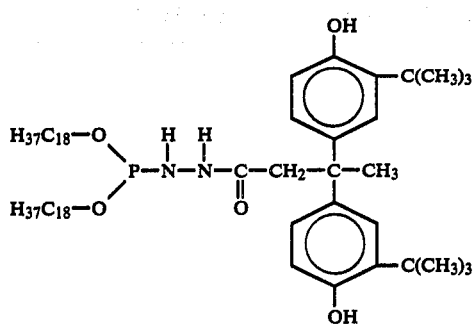

EXAMPLE 6

Phosphorous acid-octadecyl ester-octadecylamide-3,3-bis-(3'-tert.-butyl-4'-hydroxy-phenyl)-butanoyl-hydrazide This product having the formula

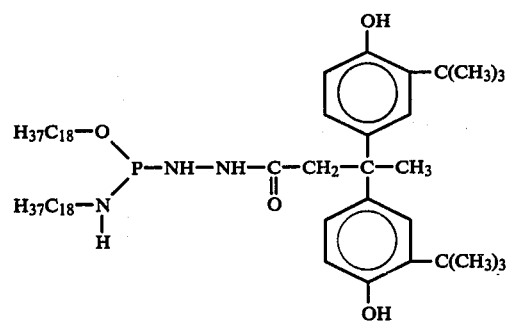

is obtained according to the process described in Example 5 from 0.2 mol each of stearyl alcohol, stearylamine, triethyl phosphite and 3,3-bis-(3'-tert.-butyl-4'-hydroxyphenyl)-butanoic acid hydrazide in the presence of traces of NaOH as basic ester interchange catalyst, while distilling off about 34 ml of ethanol. After having established reduced pressure for a short time, 105 g of a product having a melting point of 118° C. are obtained as residue.

EXAMPLE 7

Phosphorous acid-tris-[3,3-bis-(3'-tert.-butyl-4'-hydroxy-phenyl)-butanoyl-hydrazide]

The hydrazide of the formula

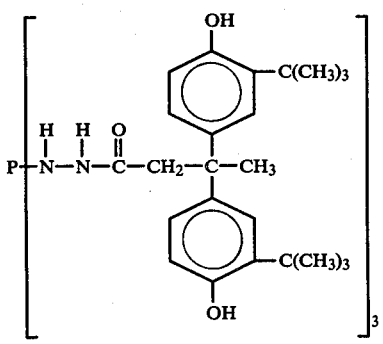

is obtained according to the ester interchange process described in Example 5 by reaction of 239 g (0.6 mol) of 3,3-bis-(3'-tert.-butyl-4'-hydroxyphenyl)-butanoic acid hydrazide with 35.2 ml (0.2 mol) of triethyl phosphite in the presence of 1 drop of triethylamine, while setting free about 34 ml of ethanol which are distilled off. Yield: 192 g of a resin having a melting point of 150° C.

EXAMPLE 8

β-Hydroxy-triacontyl-octadecyl-phosphorous acid diester-3,3-bis-(3'-tert.-butyl-4'-hydroxy-phenyl)-butanoyl-hydrazide A mixture of 79.6 g (0.2 mol) of 3,3-bis-(3'-tert.-butyl-4'-hydroxyphenyl)-butanoic acid hydrazide, 54 g (0.2 mol) of stearyl alcohol, 100 g (0.2 mol) of β-hydroxy-triacontyl alcohol, 36 ml (0.2 mol) of triethyl phosphite, and 1 drop of triethylamine are stirred under a nitrogen blanket at 140 to 180° C. until about 34 ml of ethanol are distilled off via a 20 cm Vigreux column. By establishing a water jet vacuum for a short time at a bath temperature of 180° C., the batch is liberated from traces of unreacted triethyl phosphite. The hot melt is filtered off via a steam-heated folded filter. 231 g of the following compound are obtained

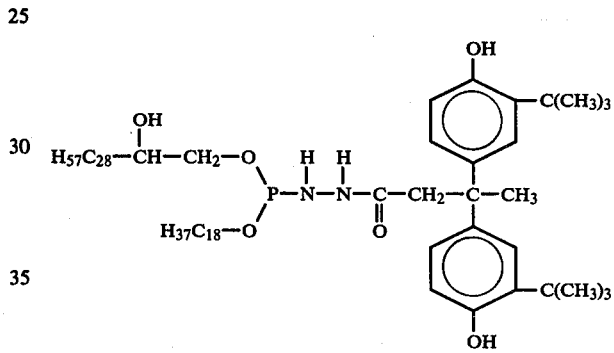

which has a melting point of 81°-85° C.

EXAMPLE 9

This Example shows the antioxidant effect of the phenol-carboxylic acid hydrazides of the invention and the derivatives thereof.

A mixture containing 100 parts by weight of non-stabilized polypropylene powder having a density of 0.90 (melt flow index is about 5 g/10 minutes, determined according to ASTM D 1238-62 T)

0.2 part by weight of calcium stearate, and 0.3 part by weight of the substance to be tested is homogenized for 5 minutes at 200° C. on a two-roll mill. Subsequently, the plastics melt is molded at 200° C. to form a plate having a thickness of 1 mm. Strip-like test specimens (100×10×1 mm) are cut from this plastics plate, put into a motor-driven device provided with rotating hurdles placed in a drying cabinet and subject to a temperature of 140° C. with uniform feed of fresh air in order to determine the resistance to ageing under heat. The period of time is recorded after which local embrittlement occurs, that is, according to German Industrial Standard DIN 53383, until formation of discolored, troubled spots where part of the material comes loose. The test results are listed in the following Table:

| Compound according to Example No. | Residence time (days) |
|---|---|
| 1 | 23 |
| 5 | 25 |
| without stabilizer (comparison) | 3 |

As the Table shows, the substances of the invention are excellent stabilizers for polyolefins.

In a further test series, the substances of the invention were tested according to the above formulation, but with addition of 0.15 part of di-octadecyl-disulfide as costabilizer. The results are listed in the following Table:

| Compound according to Example No. | Residence time (days) |
|---|---|
| 1 | 70 |
| 5 | 72 |
| without stabilizer of invention (comparison) | 37 |

This test series, too, proves the excellent activity of the substances of the invention.

What is claimed is:

1. Compounds of the formula

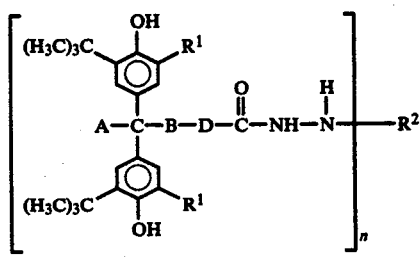

in which n is 1, 2 or 3;

A and B represent together with the carbon atom separating them a cycloalkyl ring having from 5 to 12 carbon atoms;

D is a chemical bond or a $C_1$ to $C_3$-alkylene radical and $R^1$ is H or a $C_1$ to $C_4$-alkyl radical, while $R^2$ is either (a) a hydrogen atom or (b) corresponding to the meaning of n, a mono-, bi- or tri-valent phosphorus containing radical having the structure:

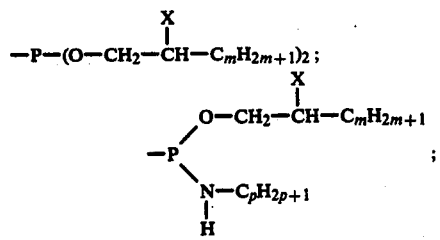

-continued

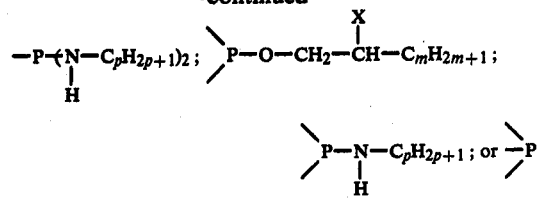

in which m is an integer of from 0 to 30, p is an integer of from 10 to 20, and x is H or OH, and in the case (b) A may also be H or $C_1$ to $C_8$-alkyl and B may also be $C_1$ to $C_8$-alkylene.

2. A process for the preparation of the phosphorus-containing compounds as claimed in claim 1, which comprises reacting esters of geminal bis-(tert.-butyl-4'-hydroxyphenyl)-alkylcarboxylic acids of the formula

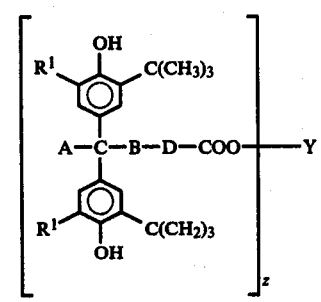

in which $R^1$, A, B and D are as defined in claim 8, Y is an alkyl or alkylene radical having from 1 to 4 carbon atoms, and z is 1 or 2 corresponding to the valency of Y, with hydrazine hydrate, and subsequently reacting n moles of the hydrazides obtained with 1 mol of a tri-lower alkylphosphite or triphenyl phosphite and altogether 3—n moles of one or several members selected from the group consisting of aliphatic monoalcohols or beta-hydroxy alcohols having from 2 to 30 carbon atoms and monoamines having from 10 to 20 carbon atoms in the presence of catalytic amounts of tertiary amines or strong bases.

3. A stabilizer combination for stabilizing polyethylene or polypropylene against degradation by light and heat, said combination consisting essentially of (a) a stabilizer compound as claimed in claim 1 and, in addition, (b) a stabilizer selected from the group consisting of phenolic antioxidants, sulfur-containing stabilizers, metal salts of higher fatty acids, phosphites, ultra-violet stabilizers and (c) mixtures of (b).

4. Stabilized polyethylene or polypropylene wherein a compound as claimed in claim 1 is contained as stabilizer.

5. Stabilized polyethylene or polypropylene as claimed in claim 4, wherein the amount of stabilizer is from 0.001 to 5.0% by weight, relative to the polymer.

6. A process for stabilizing synthetic polymers, which comprises adding as stabilizer to the polymer during polymer preparation a compound as claimed in claim 1 in an amount of from 0.001 to 5.0% by weight relative to the polymer.

* * * * *